US008921103B2

(12) United States Patent
Suggs et al.

(10) Patent No.: US 8,921,103 B2
(45) Date of Patent: Dec. 30, 2014

(54) LAMINAR CONSTRUCT FOR TISSUE-ENGINEERED DERMAL EQUIVALENT

(75) Inventors: Laura Suggs, Austin, TX (US); Shanmugasundaram Natesan, San Antonio, TX (US); Ge Zhang, Hudson, OH (US); Robert J. Christy, San Antonio, TX (US); Thomas Walters, Wimberly, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/870,128

(22) Filed: Aug. 27, 2010

(65) Prior Publication Data

US 2011/0053269 A1 Mar. 3, 2011

Related U.S. Application Data

(60) Provisional application No. 61/237,868, filed on Aug. 28, 2009.

(51) Int. Cl.
*C12N 5/00* (2006.01)
*C12N 5/02* (2006.01)
*C12N 5/10* (2006.01)
*C12N 5/071* (2010.01)

(52) U.S. Cl.
CPC ........ *C12N 5/069* (2013.01); *C12N 2502/1323* (2013.01); *C12N 5/0698* (2013.01); *C12N 2506/1384* (2013.01); *C12N 2502/28* (2013.01); *C12N 2533/56* (2013.01); *C12N 2502/094* (2013.01)
USPC ........... 435/325; 435/395; 435/397; 435/363; 435/371; 435/375; 435/377; 435/382

(58) Field of Classification Search
None
See application file for complete search history.

(56) References Cited

U.S. PATENT DOCUMENTS

| | | | | |
|---|---|---|---|---|
| 4,837,379 A | * | 6/1989 | Weinberg | 424/548 |
| 5,944,754 A | * | 8/1999 | Vacanti | 623/23.76 |
| 2011/0202142 A1 | * | 8/2011 | Mao et al. | 623/23.72 |

OTHER PUBLICATIONS

Dufourcq et al., Secreted Frizzled-Related Protein-1 Enhances Mesenchymal Stem Cell Function in Angiogenesis and Contributes to Neovessel Maturation; Stem Cells, vol. 26, pp. 2991-3001, 2008.*
Bae et al., Gene and microRNA expression signatures of human mesenchymal stromal cells in comparison to fibroblasts; Cell Tissue Research, vol. 335, pp. 565-573, 2009.*
Dietrich et al., Fine-tuning of a three-dimensional microcarrier-based angiogenesis assay for the analysis of endothelial-mesenchymal cell co-cultures in fibrin and collagen gels; Angiogenesis, vol. 9, pp. 111-125, 2006.*
Zhang et al., A PEGylated Fibrin Patch for Mesenchymal Stem Cell Delivery; Tissue Engineering, vol. 12, No. 1 pp. 9-19, 2006.*
Moioli et al., Synergistic Actions of Hematopoietic and Mesenchymal Stem/Progenitor Cells in Vascularizing Bioengineered Tissues; PLoS one, vol. 3, No. 12, e3922, pp. 1-11, 2008.*
Ball et al., Vascular endothelial growth factor can signal through platelet-derived growth factor receptors; Journal of Cell Biology, vol. 177, No. 3, pp. 489-500, 2007.*
Kim et al., Effects of human amniotic membrane grafts combined with marrow mesenchymal stem cells on healing of full-thickness skin defects in rabbits; Cell Tissue Res, vol. 336, pp. 59-66, 2009.*
Sasaki et al., Mesenchymal Stem Cells are Recruited into Wounded Skin and Contribute to Wound Repair by Transdifferentiation into Multiple Skin Cell Type; Journal of Immunology; vol. 180, pp. 2581-2587, 2008.*
Arthur et al., The Therapeutic Applications of Multipotential Mesenchymal/Stromal Stem Cells in Skeletal Tissue Repair; J Cellular Physiology, vol. 218, pp. 237-245, 2009.*

* cited by examiner

*Primary Examiner* — Jennifer Dunston
*Assistant Examiner* — Addison D Ault
(74) *Attorney, Agent, or Firm* — Reed Smith LLP; Robert R. Riddle

(57) ABSTRACT

Compositions and methods for creating a laminar construct for tissue-engineered dermal equivalent are provided. One composition provided herein comprises a hydrogel matrix comprising two or more hydrogels layers and a population of stem cells. Associated methods are also provided.

7 Claims, 15 Drawing Sheets

FIG. 7A-H
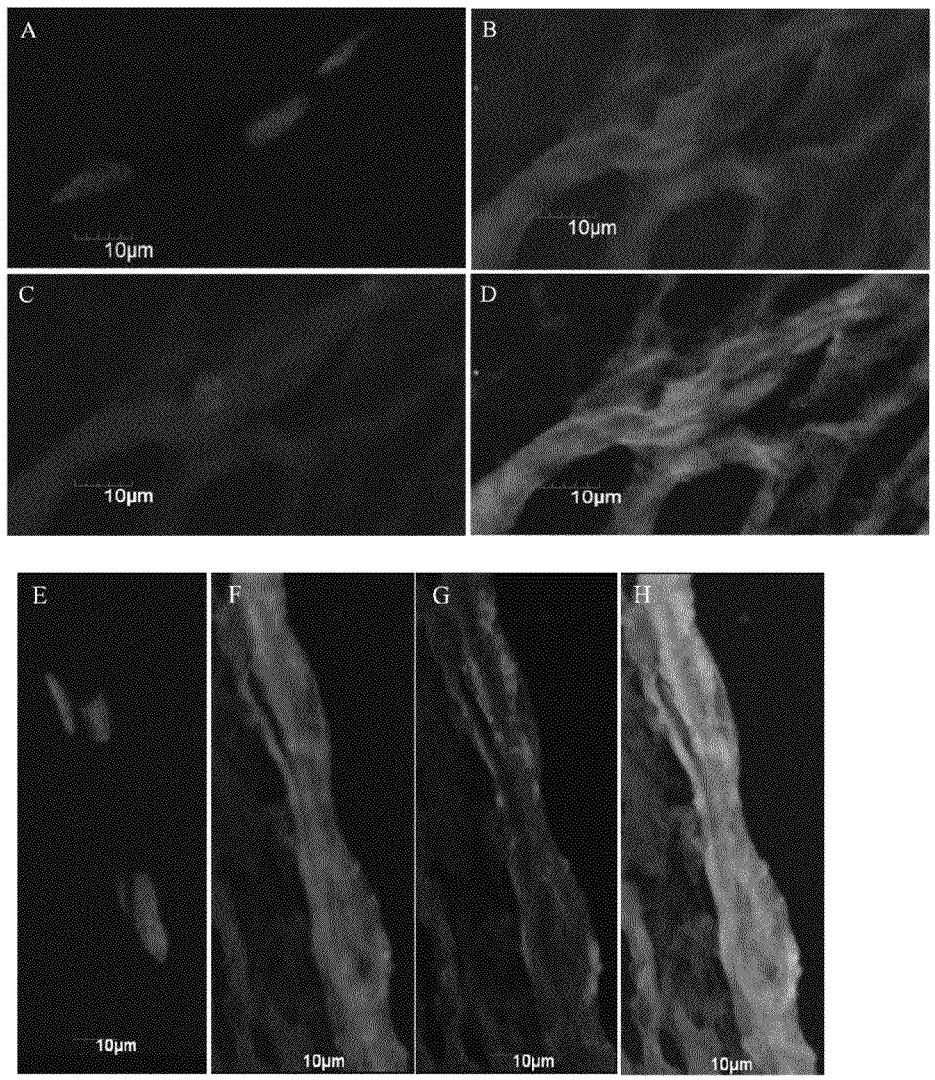

FIG. 7I-L
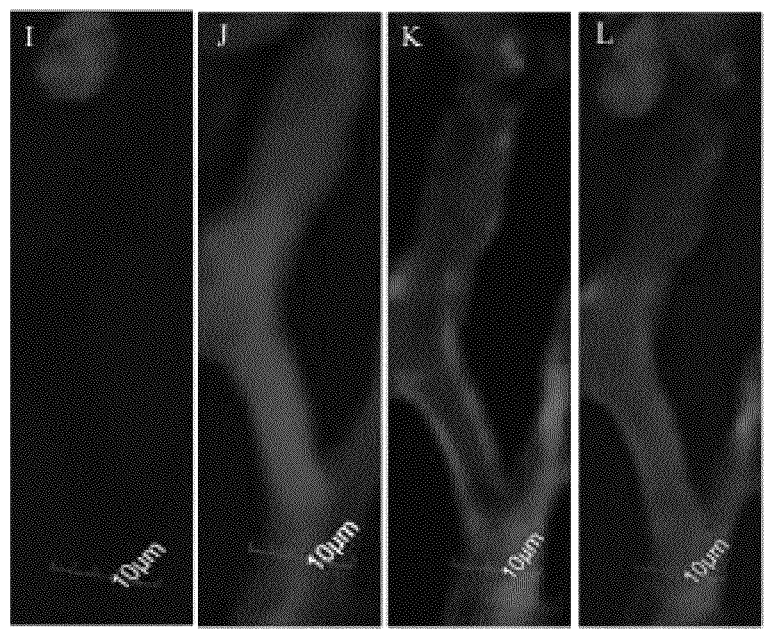

Phenotypic Changes of ASC During Differentiation in 3-D Collagen Gel

Section Showing ASC Differentiated to Epithelial Like
Cells in 3-D Collagen Gel Express Pancytokeratin Section Showing ASC Differentiated to Epithelial
Like Cells in 3-D Collagen Gel Express Krt10

LAMINAR CONSTRUCT FOR TISSUE-ENGINEERED DERMAL EQUIVALENT

CROSS REFERENCE TO RELATED APPLICATIONS

This application claims priority to U.S. Provisional Application No. 61/237,868, filed Aug. 28, 2009.

STATEMENT OF GOVERNMENT INTEREST

This invention was made with government support under Grant Number W81XWH-08-C-0062 awarded by the US Army Medical Research and Materiel Command. The government has certain rights in the invention.

BACKGROUND

Skin grafts are often necessary for the treatment of severe, full-thickness burns, non-healing skin ulcers and other surgical operations where there is loss of skin or a need for skin coverage of soft tissue. The graft procedure involves placing a layer of healthy skin on the wound site. The graft serves to close the wound, protecting the underlying tissue to facilitate healing. Two main classifications of skin graft surgery, autograft and allograft, depend on the source of the donor tissue. In an autograft operation, the skin graft is harvested from a different location on the patient. In an allograft operation, the graft is harvested from an external source such as another donor (e.g., cadaver) or is prepared artificially (e.g., dermal equivalent).

Previous work done in the field of tissue engineering has produced skin grafts that may be used in surgery. Generally, the tissue graft may be produced by seeding a collagen matrix or other biocompatible material with the appropriate cells to create the desired culture. As the cells proliferate, the matrix degrades and is eventually replaced by a layer of healthy tissue. This layer of tissue or the matrix seeded with cells may be used in skin graft surgery.

Recent advances in tissue engineering based wound dressings have resulted in the emergence of a range of dermal, epidermal and even complete skin equivalents. Advances in cellular biology and knowledge in wound healing and growth factors have provided a wide variety of choices to attack the problem of the complex wound. Continued research and new developments have improved the level of care in the field of complex burn wound care and has resulted in the availability of epidermal, dermal and total skin substitutes.

For example, Epicel, a cultured epidermal autograft (CEA), is one of the early tissue engineered products. It is an epidermis cultured in vitro and not a true skin equivalent which may limit its range of potential uses. CEA requires several weeks to produce, has a low rate of graft take, is very fragile, is susceptible to infection, and is not suitable for use without a dermal layer. To address the above problems, composites consisting of dermal equivalents in combination with epidermal components were developed. A typical engineered skin substitute (ESS) is composed of an epidermal substitute of autologous keratinocytes, attached to a dermal analogue of collagen or collagen-glycosaminoglycan combination populated with autologous fibroblasts. Following in vitro culture prior to grafting, ESS demonstrates morphogenesis similar to native human skin.

However, current efforts to produce suitable dermal equivalents are complicated by the multiple layers and corresponding functions that must be present. For example, the external layer must be capable of closing the wound and providing protection to the underlying tissue. Internal layers must be conducive to the formation of blood vessels and circulation. The state-of-the-art techniques in tissue engineered skin rely on the sequential culture of dermal fibroblasts and keratinocytes on a collagen matrix. The culture process relies on a relatively long culture time to increase cell numbers within the construct before a suitable dermal equivalent has been produced.

SUMMARY

The present disclosure generally relates to laminar constructs and more specifically, to laminar constructs for tissue-engineered dermal equivalents.

In one embodiment, the present disclosure provides a laminar construct comprising a hydrogel matrix comprising at least a first hydrogel layer and a second hydrogel layer, and a plurality of mesenchymal stem cells.

In another embodiment, the present disclosure provides a method of creating a laminar construct comprising: providing a hydrogel matrix comprising at least a first hydrogel layer and a second hydrogel layer, and introducing a plurality of mesenchymal stem cells to the hydrogel matrix.

In yet another embodiment, the present disclosure provides a method comprising preparing a dermal equivalent for an allograft operation for a patient, wherein the dermal equivalent comprises a hydrogel matrix comprising at least a first hydrogel layer and a second hydrogel layer, and a plurality of mesenchymal stem cells.

The features and advantages of the present invention will be readily apparent to those skilled in the art. While numerous changes may be made by those skilled in the art, such changes are within the spirit of the invention.

DRAWINGS

A more complete understanding of this disclosure may be acquired by referring to the following description taken in combination with the accompanying figures in which.

Figure 4:
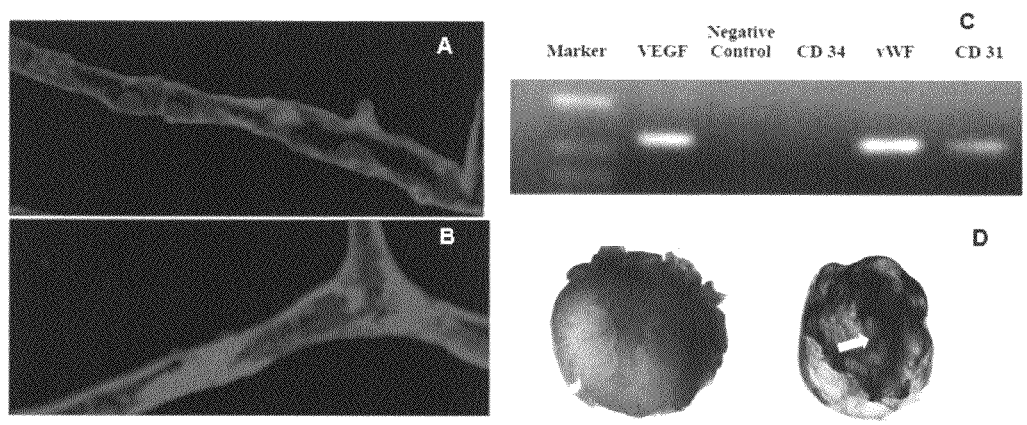

FIGS. 4A and 4B depict immunohistochemical staining against CD31 and vWF, respectively, of human MSCs embedded in PEGylated fibrin after 7 days. The images use nuclear counterstain with DAPI (20×). FIG. 4C depicts PCR showing that entrapped MSCs highly expressed VEGF and vWF (lane 2 and 5), expressed CD31 (lane 6), but did not express CD 34 (lane 4). FIG. 4D depicts a gel plug assay using 1 ml preformed gel plugs after a 7 day subcutaneous implant. The left image is fibrin gel only while the right is PEGylated fibrin. The arrow denotes blood vessel in the gel interior.

Figure 5:
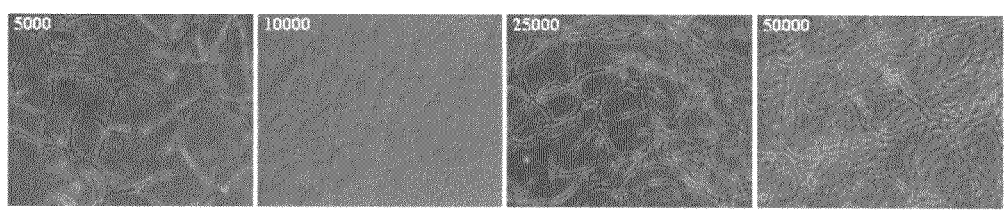

FIG. 5 depicts the differentiation of ASC into vascular like structures in PEGylated fibrin.

Figure 6:
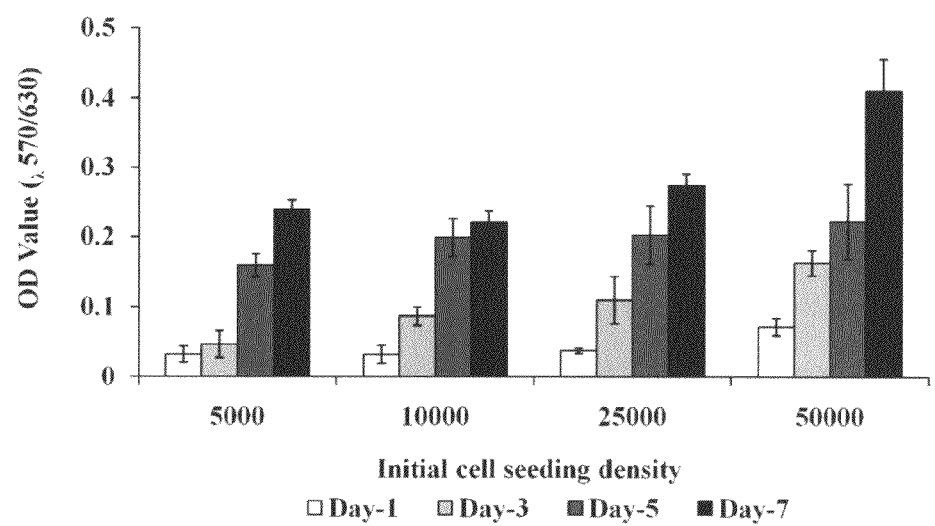

FIG. 6 depicts the proliferation timecourse of ASC in PEGylated fibrin.

FIGS. 7A-7L depict Confocal Z-stacked images of tube-like structures formed by ASC in PEGylated fibrin gel. ASC when seeded in PEGylated fibrin exhibit an endothelial phenotype expressing both von Willebrand factor (B) and CD31 (C). FIG. 7D shows the merged image of 7B and 7C stained with Hoeschst (D) for nuclei. The formed tubes were positive for both pericyte specific markers NG2 (G) and α-SMA (FIG. 7K) and the endothelial cell specific marker von Willebrand factor (7F and 7J). FIGS. 7H and 7L shows von Willebrand factor and Hoeschst (7E and 7I) merged with NG2 and α-SMA, respectively.

Figure 8:
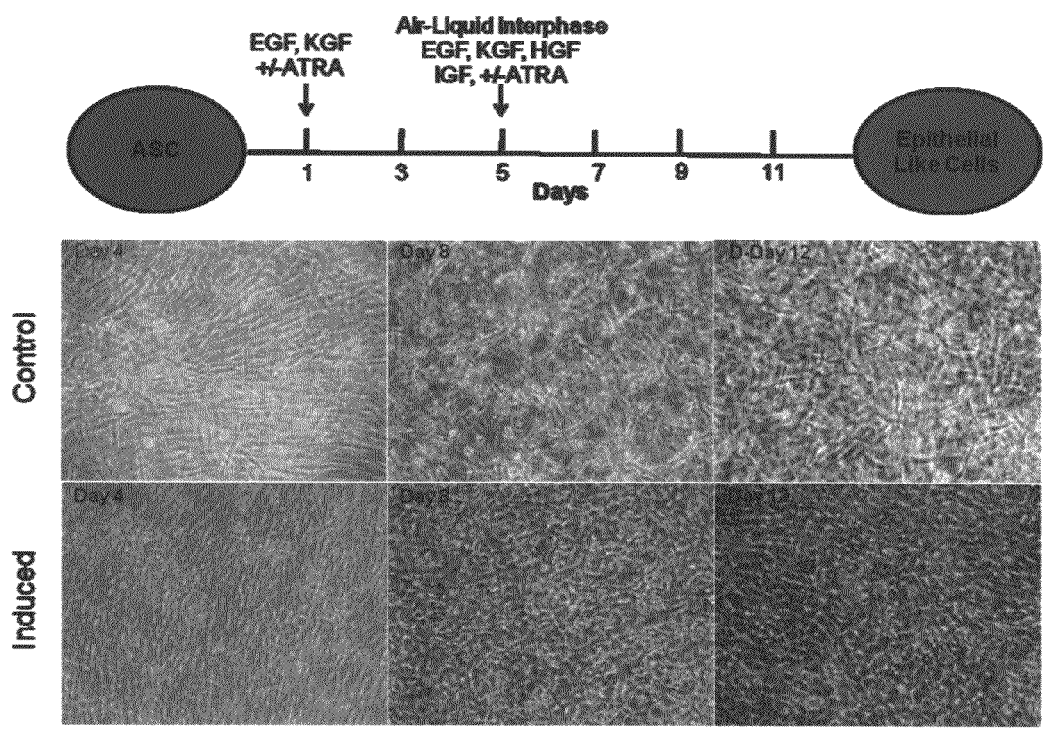

FIG. 8 depicts a schematic representation of the differentiation strategy of ASC. Light micrographs are shown that were taken at various days of ASC differentiated to epithelial like cells. Control (Top), differentiated ASC (bottom).

Figure 9:
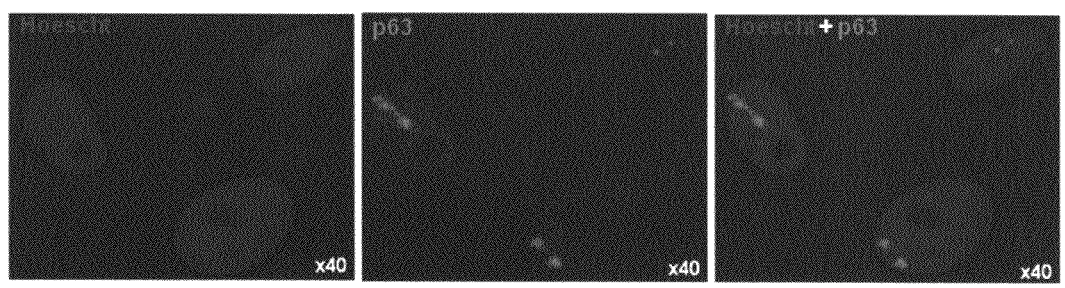

FIG. 9 depicts isolated ASC that were analyzed by immunohistochemistry and expressed p63.

Figure 10:
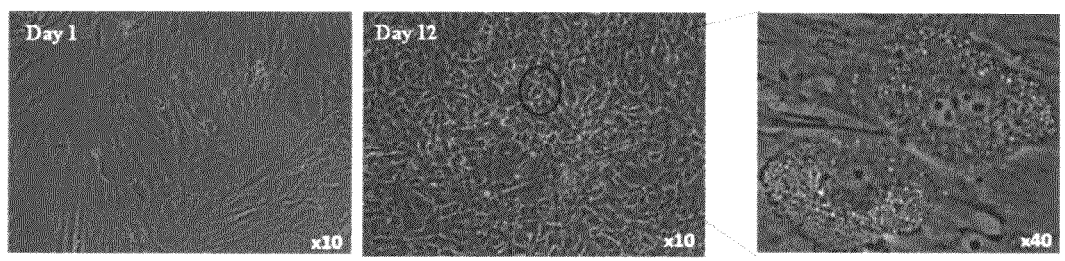

FIG. 10 depicts cells that were subjected to keratinocyte differentiation and expressed a deep granulated appearance.

Figure 11:
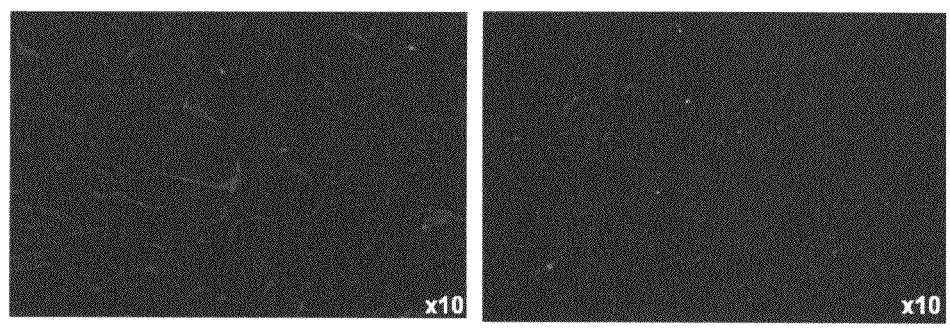

FIG. 11 depicts the staining for Pan-cytokeratin and cytokeratin 18 of cells cultured in complete media (GFs).

Figure 12A:
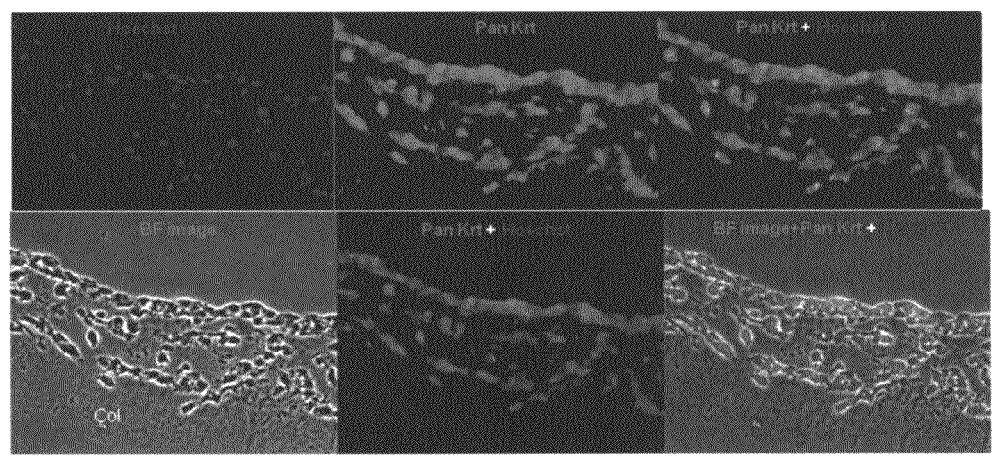
Figure 12B:
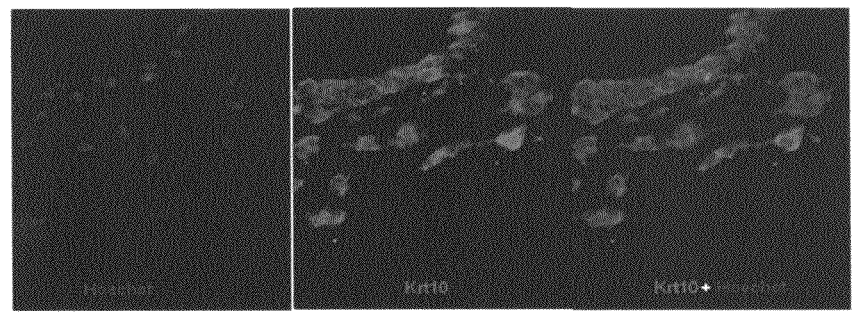

FIGS. 12A and 12B depict sections showing differentiated ASC to organize like an epithelial layer over collagen matrix (A; col-collagen). Immunofluorescence image of section showing positive for pan cytokeratin (B) and krt 10 (C) (Alexa fluor 594 and Hoeschst overlay).

Figure 13:
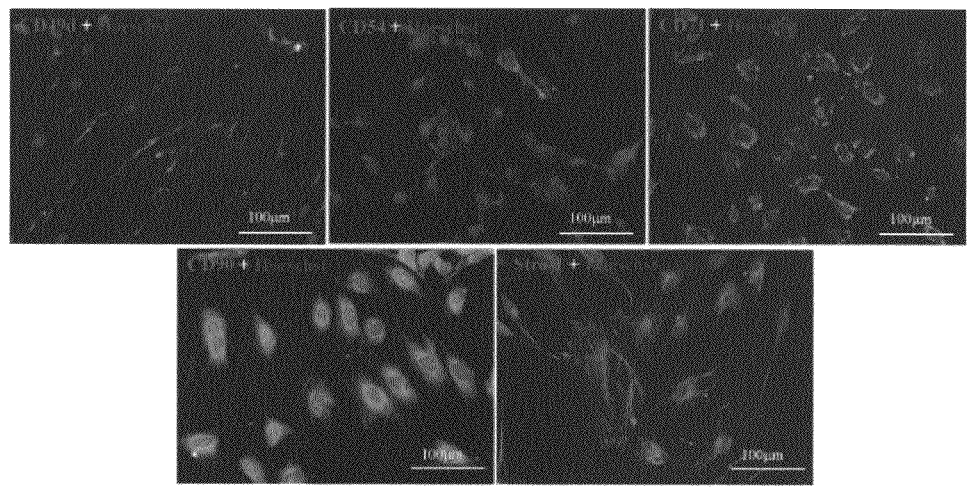

FIG. 13 depicts the immunocytochemical analysis of ASC isolated from rats. Photomicrographs are of markers expressed in third passage ASC. Figures in each panel indicate the specific cell surface marker. All antibodies, except Stro-1, are FITC-labeled primary antibodies. Stro-1 is identified using isotype matched FITC-labeled rat IgM. All photomicrographs at ×20 magnification.

Figure 14:
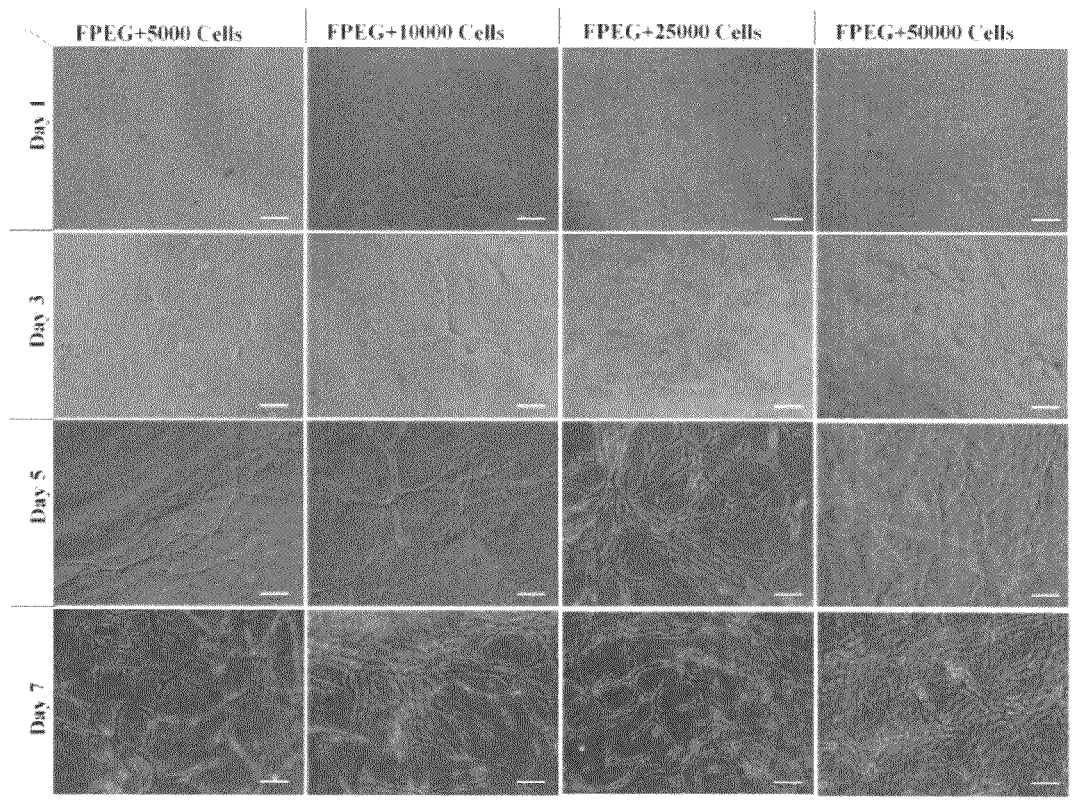

FIG. 14 depicts light microscopic images of differentiation time-course of ASC into vascular like structures. Cells began to form vascular tube-like networks in the PEGylated fibrin gel in the absence of additional soluble cytokines. The amount of network formation was related to the initial cell density. (Scale bar=100 μm)

Figure 15:
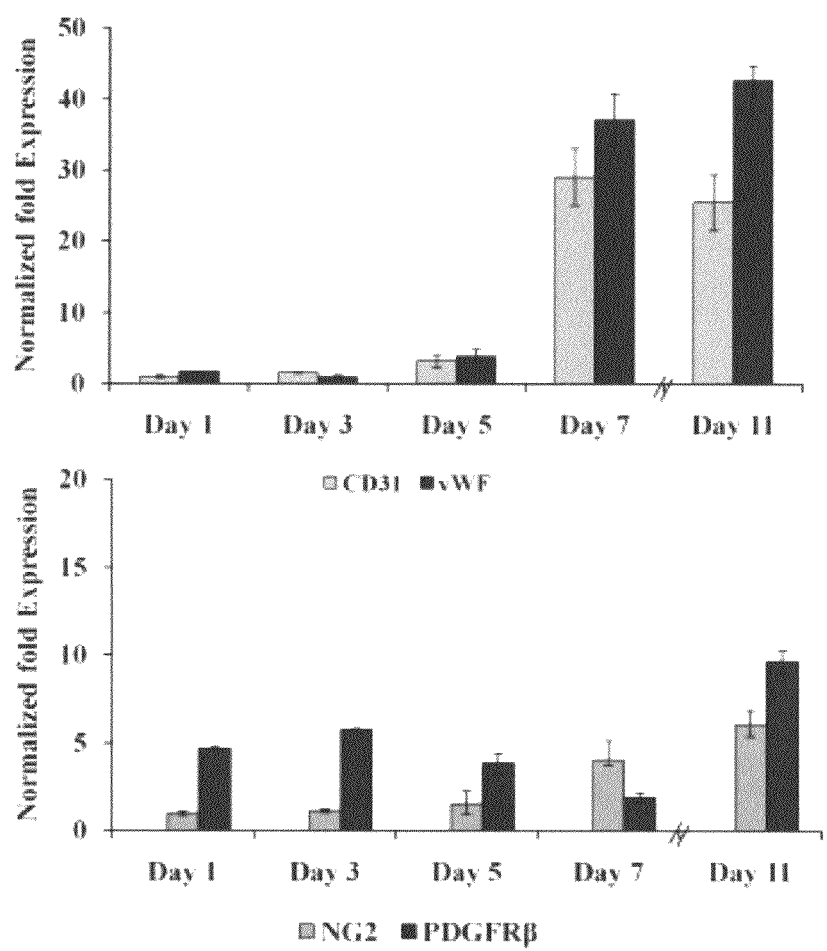

FIG. 15 depicts endothelial and pericyte specific markers expressed by the differentiated ASC in PEGylated fibrin gels. Expression levels of endothelial cell specific markers (CD31, von Willebrand factor) and pericyte specific markers (NG2 and PDGFRβ) were analyzed using Real Time Polymerase Chain Reaction (RT-PCR). There was significant increase in endothelial cell specific markers; CD31 (25 fold) and vWF (42 fold) in comparison to pericyte markers; NG2 (6 fold) and PDGFRβ (9 fold) by day 11.

FIGS. 16A-16F are images depicting ASC released from chitosan microspheres in vitro in PEGylated fibrin and collagen gels. Phase contrast images of ASC migrated from chitosan microspheres into collagen (A, B and C) and PEGylated fibrin (D, E and F). ASC that have migrated from CSM attached to the PEGylated fibrin shows classical sprouting (A, day 2) followed by differentiating into tube-like structures (B, day 5). Over the time course of differentiation, they migrate into the gel forming a dense multicellular network (Day 8, C). ASC released from the CSM into collagen were more spindle in appearance (Day 2, D) which developed filopodias (Day 6 E). Over time they formed more elongated morphological structures stretching along fibril assemblies resembling cells that are associated with stromal tissues.

FIGS. 17A-17F are images depicting Qdot 565 labeled ASC tracked after migration from chitosan microspheres after Day 6 into PEGylated fibrin and collagen gels. Epifluorescent images of Qdot 565 labeled ASC tracked after migration from the CSM into PEGylated fibrin (A-C) and collagen (D-F) after 6 days. ASC released from chitosan microspheres into both PEGylated fibrin and collagen could be tracked (A and D) over 6 days. Cells forming tubes-like structures (B) in PEGylated fibrin and striated morphologies (E) were colocalized with Qdot 565 (C and F).

FIGS. 18A-18H are images depicting the bidirectional differentiation of ASC in the PEGylated fibrin—(ASC-CSM)—collagen gel constructs. ASC loaded in CSM exhibited matrix driven phenotypic changes into a fibroblast-like morphology in the collagen layer (A, C, E and G) and a tube-like morphology in the PEGylated fibrin layer (B, D, F and H) simultaneously. ASC started to migrate into both the gels on Day 3 (A and B) and proliferated as a fibroblast-like phenotype in collagen (C) and tube-like sprouts (D) in PEGylated fibrin on day 5. By day 7 the collagen layer showed an increase in fibroblast-like cells (E) which eventually populated the gels by day 11 (G). In the PEGylated fibrin layer the sprouts started to form long networks by day 7 (F) which formed complex networks by day 11 (H).

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

The present invention discloses a laminar construct for tissue-engineered dermal equivalents. By applying the teachings of this disclosure, a person of ordinary skill in the art would be able to create a multi-layered tissue culture from a single source of stem cells. The present teachings allow for the formation of both blood vessels and dermal connective tissue from a uniform cell population that may be seeded and spontaneously assemble into the desired layers without the need for long culture times that are necessary when multiple layers are cultured sequentially. This tissue culture is useful as a dermal equivalent or tissue-engineered skin.

In one embodiment, a laminar construct of the present disclosure comprises a hydrogel matrix and a population of mesenchymal stem cells (MSC). Stem cells are unique among cells that may be cultured because they are not constrained to a particular cell type. Rather, stem cells from a single source are capable of differentiating into a variety of distinct cell types depending on their environment and other external factors. External factors may include soluble signals, insoluble or matrix molecules or other cell types. Soluble signals include, but are not limited to, growth factors, hormones and bioactive small molecules. Matrix molecules include, but are not limited to, fibrous proteins such as collagen and elastin, adhesion proteins such as fibronectin and laminin as well as glycosaminoglycans such as hyaluronic acid or chondroitin sulfate either alone or complexed as a proteoglycan. In fact, a single source of stem cells may differentiate into multiple types of tissue depending upon the properties of the hydrogel matrix that surround an individual stem cell. In certain embodiments, the hydrogel matrix may be engineered to control cell differentiation in the absence of growth factor supplementation of culture media.

The population of stem cells may be sourced from multiple locations in the human body including, but not limited to, fat, bone marrow, blood and muscle. Mesenchymal stem cells derived from adipose tissues (ASC) differentiate into multiple phenotypes including adipose, muscle, bone, neuronal, endothelial, hepatocyte and epithelial-like cells. Adipose tissue is an attractive in vivo cellular source of autologous stem cells for regenerative therapies for several reasons. Adipose-derived stem cells may be easily isolated from the stromal vasculature of subcutaneous adipose tissue by liposuction with a minimally invasive procedure and the excised adipose contains 100 to 1000 times more pluripotent cells per cubic centimeter than bone marrow. In certain embodiments, the population of stem cells may be sourced from the patient or a donor. The stem cells may be harvested by any method or technique known in the art.

The laminar construct also comprises a hydrogel matrix. In some embodiments, the hydrogel matrix comprises two or more hydrogel layers. One possible hydrogel layer may comprise a material that encourages stem cell differentiation towards blood vessel cells. Examples of such hydrogel layers include, but are not limited to, hydrogels comprising fibrin, PEGylated fibrin, hyaluronic acid and soluble degradation products thereof. Hydrogels suitable for use in the present disclosure may also comprise matrix molecules along with soluble signals known to encourage blood vessel in-growth during inflammation and wound healing. PEGylated fibrin exhibits several unique features of both synthetic hydrogels and natural materials. First, the presence of PEG provides a highly hydrated (>90% water) moist environment for managing exudate. The presence of fibrin confers biodegradability to the material; however, PEGylated fibrin is potentially more stable in vitro than fibrin alone. Finally, the inherent biologic activity of fibrin stimulates tissue and blood vessel in-growth.

Additionally, a layer of the hydrogel matrix may comprise a material that encourages stem cell differentiation towards dermal fibroblasts. This type of material includes, but is not limited to, types I, II, III, IV and V collagen; adhesion proteins such as fibronectin, tenascin and vitronectin; glycosaminoglycans such as chondroitin sulfate, heparan sulfate and hyaluronic acid as well as provisional matrix proteins including fibrin-based materials or combinations thereof.

The hydrogel matrix may be created by any method or technique known in the art. For example, PEGylated fibrin may be created by modifying fibrinogen (Fgn) with the benzotriazole carbonate derivative of polyethylene glycol to create secondary crosslinking. Specifically, a derivatized polyethylene glycol (PEG) has end groups that may react with peptide side chains such as amine, hydroxyl, carboxyl or thiol functionalities. The derivatized PEG is typically a carbonate, N-hydroxysuccinimide ester, epoxide, or tresylate group. The reaction of derivatized PEG with proteins may be performed under relatively mild conditions at room or body temperature in aqueous solution at pH values typically between 6.0 and 8.0. Reaction times are dependent on the reactivity of the PEG end groups and may proceed for between 5 minutes to several hours. Potential amine-reactive PEG derivatives include, but are not limited to, benzotriazole carbonate PEG, succinimidyl methylbutonoate PEG, succinimidyl propionate PEG, nitrophenyl carbonate PEG, succinimidyl carbonate PEG, succinimidyl succinate PEG, succinimidyl glutarate PEG, and succinimidyl valerate PEG. In a preferred embodiment, an end-group hydrolysis rate of about 20 minutes is used.

Figure 1:
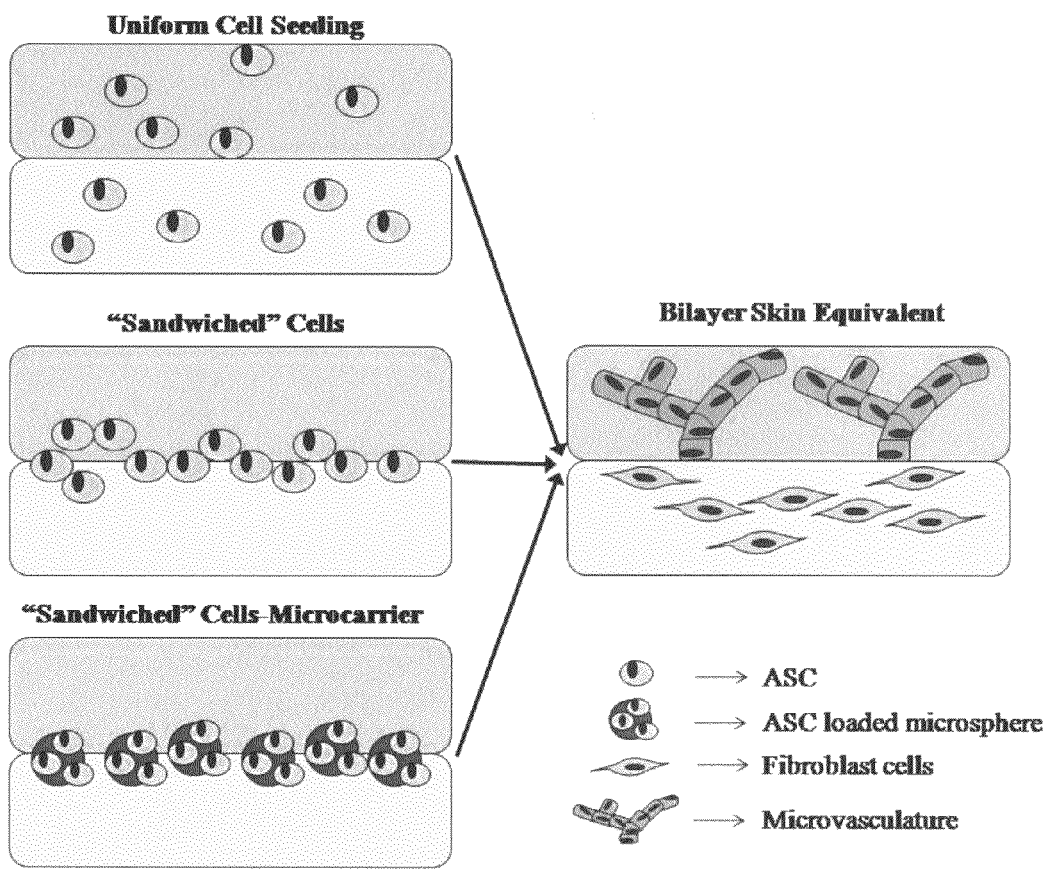
FIG. 1 illustrates the creation of a bilayer dermal construct, according to one embodiment.
Figure 2:
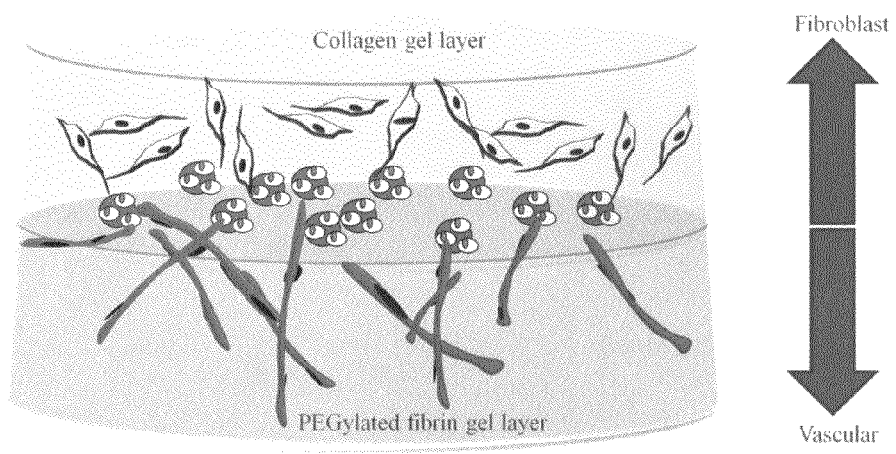
FIG. 2 is a schematic of a layered construct according to one embodiment which could provide both the vascular as well as dermal fibroblast component for treatment of wounds.
Figure 3:
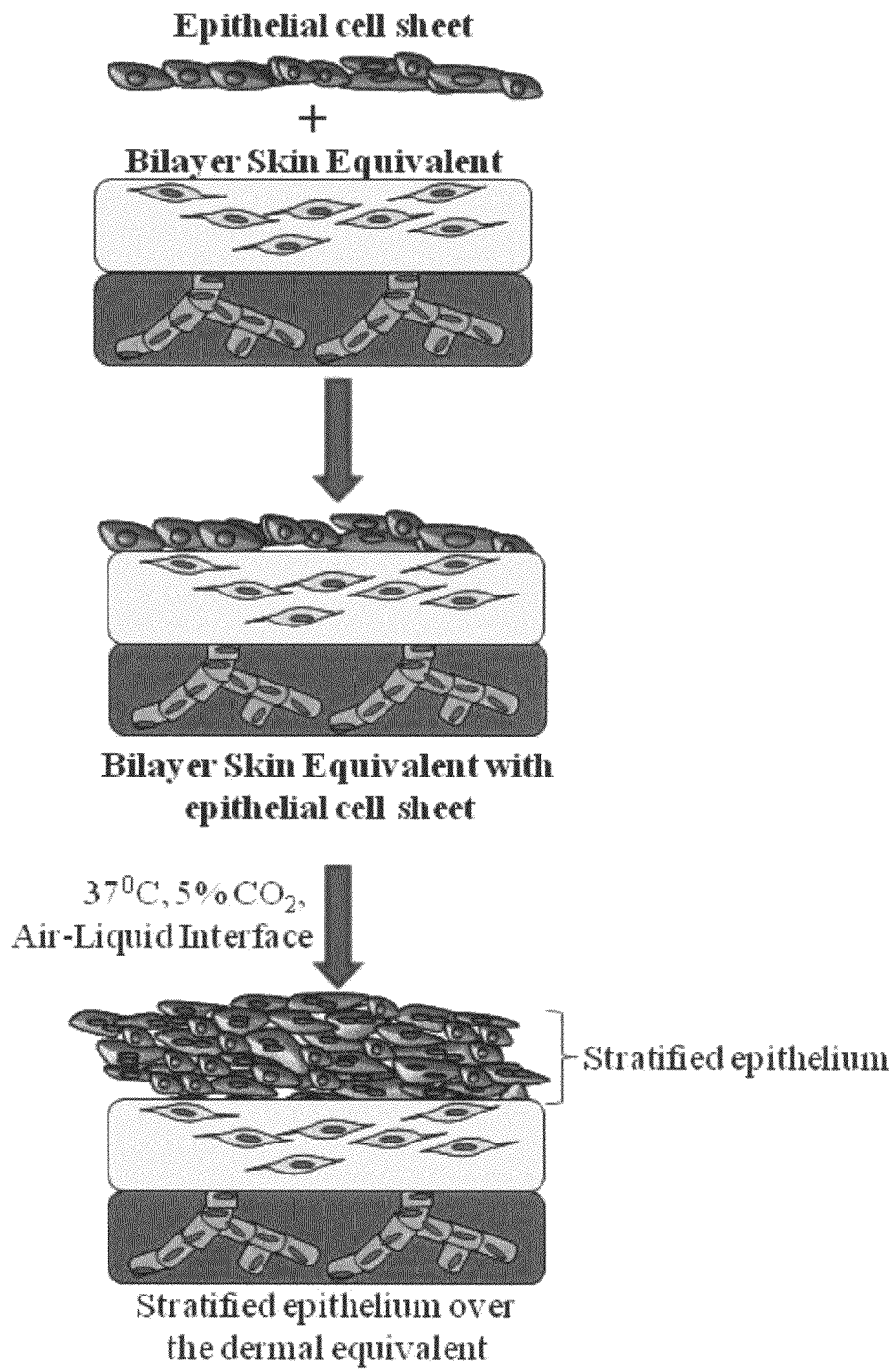
FIG. 3 illustrates the creation of a laminar skin equivalent, according to one embodiment.

Once sourced, the stem cells of the present disclosure may be combined with the hydrogel matrix in a variety of ways. In one embodiment, these stem cells may be sandwiched between the two or more hydrogel layers. In another embodiment, the stem cells may be seeded uniformly within the hydrogel layers prior to gellation of the matrix. The stem cells may be seeded from suspension or following culture on microcarrier beads, such as chitosan microspheres. In a preferred embodiment, the cells are seeded on microcarriers and "sandwiched" between two hydrogel layers as shown in FIGS. 1 and 2.

The present disclosure presents a number of advantages over existing techniques. For example, if the stem cells are sourced from an individual patient, the process results in an autograft with fewer immune complications. Simpler production results from inducing the cells to differentiate towards different cell types, including but not limited to vascular and dermal cells, via properties of the hydrogel matrix rather than the culture conditions. Additionally, the present disclosure provides for the formation of blood vessels within the structure which may increase the viability of the construct. One limitation, the lack of epidermal (keratinocyte) cell population, may be overcome through in-growth or via split-thickness grafts.

To facilitate a better understanding of the present invention, the following examples of certain aspects of some embodiments are given. In no way should the following examples be read to limit, or define, the entire scope of the invention.

EXAMPLE 1

From previous work, it has been demonstrated that MSCs by themselves cannot differentiate into cells expressing EC phenotype without induction by the appropriate cytokines Endothelial cell tubes in Matrigel™ typically disappear within a few hours. However, in PEGylated fibrin gel, MSCs maintained vascular tube-like networks until the gel degraded, approximately 7-10 days later. Murine, porcine and rat MSCs may also be capable of forming tubes within the PEGylated fibrin gels. Controls of unreactive PEG mixed with fibrinogen demonstrate CD31 and vWF negative phenotype. In addition to the effects that can be realized from embedded MSCs in PEGylated fibrin gels, the gels alone are able to support capillary ingrowth in a subcutaneous implantation in Lewis rats. FIGS. 4A-4D illustrate the results of embedding human MSCs in PEGylated fibrin. FIG. 4D compares fibrin gels alone after a 7 day gel plug implantation relative to the PEGylated fibrin gels. The PEGylated fibrin clearly supports extensive capillary in-growth.

EXAMPLE 2

Having seen that PEGylated fibrin gel can induce robust tube-like differentiation of mesenchymal stem cells, it was further investigated whether adipose derived stem cells (ASC) could differentiate into a typical vascular network. Advantages of using ASC are that they can be easily isolated from the stromal vasculature of subcutaneous adipose tissue by liposuction with minimally invasive procedures and the excised adipose is enriched in progenitor cells relative to bone marrow. Recent studies provide evidence that infused ASC in vivo are nonimmunogenic even when used in immunocompetent animals. Adipose derived stem cells when delivered to tissue defects elicit tissue regeneration by paracrine activation of host cells through secretion of growth factors, autocrine signaling or through direct cell-cell interactions.

Preliminary investigations show that ASC were able to form robust tube like structures as shown in FIG. 5. Within 7 days ASC were able to form dense vascular structure within PEGylated fibrin matrix, with initial seeding density of 50000 cell/ml of PEGylated solution, and showed almost a linear increase in proliferation. See FIG. 6. Certain endothelial cell specific markers including vWF and CD 31 were positively identified. The amount of vascularization was related to the initial cell number plating density. Accordingly, cell proliferation and viability increased with increasing cell seeding density, as shown in FIG. 6. Additional preliminary data indicate that, in the case of embedded ASC, cells do exhibit positive staining for pericyte markers such as smooth muscle alpha-actin (sma-actin) and NG-2 (chondroitin sulfate proteoglycan). Sees FIGS. 7A-7L. This early result provides evidence for the existence of a differentiated cell occupying a pericyte fate during ASC culture in PEGylated fibrin. In addition they also exhibited endothelial specific markers, including vWF and CD31.

EXAMPLE 3

ASCs may be differentiated into epithelial lineages and used for the production of a skin substitute. Previous studies show that mesenchymal stem cells infiltrate into a wound site and transdifferentiate into endothelial, and stromal like populations. This example describes a method to differentiate adipose derived stem cells into epithelial like cells and analyzed the expression of lineage specific cytokeratin markers.

Adipose derived stem cells were isolated using methods known in the art. The pelleted stromal cells were plated and attached cells propagated. Passage 3 cells were characterized for their immunophenotype and subjected to differentiation into epithelial cells. The differentiation media consisted of low glucose DMEM and either one or more growth factors including: keratinocyte growth factor (KGF), epidermal growth factor (EGF), hepatocyte growth factor (HGF), insulin like growth factor (IGF) with or without all trans retinoic acid (ATRA) and with or without peroxisome proliferator-activated receptor (PPAR) agonists such as fenofibrate. FIG. 8 is a schematic representation of differentiation strategy adopted in this procedure. The cultures were monitored for differentiation and harvested for analysis at day 12.

The morphology of the ASC undergoing differentiation into keratinocytes was observed by light microscopy and differentiated cells were analyzed using immunohistochemistry to monitor the differentiation into epithelial cells using standard protocols. (See FIG. 8). The isolated ASC expressed standard stem cell markers (e.g., Strol-1, CD71, CD54, Sca-1). They also expressed p63, as shown in FIG. 9, a nuclear transcription factor that has been shown to be essential for the commitment of a simple ectoderm to epidermal lineages, maintenance, and differentiation. Cells subjected to keratinocyte differentiation media exhibited the squamous structure with deep granulated appearance by day 12, as shown in FIG. 10, while cells that were in control media did not differentiate. Cells cultured in complete media (GFs) differentiated and stained positive for Pan-cytokeratin and cytokeratin 18, intermediate filament proteins responsible for the structural integrity of epithelial cells. See FIG. 11.

The differentiation ability of adipose derived stem cells using a combination of growth factors and retinoic acid provides a system for development of epidermal equivalents using appropriate biomaterial constructs.

EXAMPLE 4

Materials and Methods

Isolation of Adipose Derived Stem Cells

Rat adipose mesenchymal stem cells (ASC) were isolated from perirenal and epididymal adipose tissue using methods known in the art. Perirenal and epididymal adipose tissue was collected and washed with sterile Hanks buffered balance solution (HBBS) containing 1% bovine serum albumin (BSA). The tissue was minced, transferred into 25 ml of HBBS and centrifuged (500×g at room temperature for 10 min). The free floating adipose tissue layer was collected, transferred to 25 ml of HBSS containing 1% Fetal Bovine serum (FBS) and 200 U/ml of collagenase type II (Sigma-Aldrich, St. Louis, Mo.) for 45 minutes at 37° C. in an orbital shaker. The digested tissue was then filtered through 100 μm and 70 μm nylon mesh filter, centrifuged for 10 minutes, 500×g at room temperature, washed twice with sterile HBBS. The cell pellet was re-suspended in growth media (MesenPRO RS™ Basal Medium, supplemented with MesenPRO RS™ Growth Supplement, antibiotic-antimycotic (100 U/ml of Penicillin G, 100 μg/ml streptomycin sulfate and 0.25 μg/ml Amphotericin B) and 2 mM L-Glutamine (GIBCO, Invitrogen, Carlsbad, Calif.). Cells were cultured on T75 flasks (BD Falcon, Franklin Lakes, N.J.) and maintained in a 5% CO2 humidified incubator at 37° C. Passage 2-4 ASC were used for all experiments.

Immuncytochemistry of Stem Cell Surface Markers

ASC were incubated on a 2-well chambered slide (Nalge Nunc, LabTek® chamber slide, Noperville, Ill.) for 48 hours. The cells were washed twice with sterile HBSS, fixed with 4% paraformaldehyde for 15 minutes. Fc receptor mediated blocking sites were blocked by incubating the cells for 20 minutes with (1 μg/104 cells) of BD Fc Block™ Solution (BD Bioscience, San Jose, Calif.) or non-permeant blocking solution containing 5% donkey serum (Sigma, St. Louis, Mo.) in HBSS. Stem cell surface markers were identified by incubating ASC overnight, 4° C., with 10 μg of fluorescein isothiocytnate (FITC) conjugated anti-mouse monoclonal antibodies against CD54 (ICAM-1), CD71 (transferrin receptor), CD 49d (integrin α4) and CD90 (Thy-1 glycoprotein) (BD Bioscience, San Jose, Calif.). To observe STRO-1 (R&D Systems, Minneapolis, Minn.) expression, cells were fixed with 4% paraformaldehyde for 15 minutes, washed twice with phosphate-buffered saline (PBS), blocked with 2% serum and incubated overnight at 4° C. with 10 μg of STRO-1. The cells were washed twice with PBS and incubated 45 minutes at 4° C. with 5 μg/ml of FITC labeled anti-mouse IgM secondary reagent (R&D Systems, Minneapolis, Minn.). Non-specific fluorescence was determined using ASC incubated with FITC labeled Ig class secondary antibody reagents.

Preparation of ASC Seeded PEGylated Fibrin Gel

PEGylated fibrinogen was prepared as per our previous procedure with slight modification. BTC-PEG-BTC (benztriazole modified polyethylene glycol, 3400 Da, Nektar, San Carlos, Calif.) was added to fibrinogen (Sigma-Aldrich, St. Louis, Mo.) in a concentration ratio of 1:10, BTC-PEG-BTC: Fibrinogen, in tris-buffered saline (TBS), pH 7.8, and incubated for 20 minutes at 37° C. An equal volume of thrombin (Sigma-Aldrich, St. Louis, Mo.) in 40 mM $CaCl_2$; and a final concentration of 100 U/ml was added and incubated for 10 minutes at 37° C. The resulting gels were then rinsed with TBS (pH 7.8) to remove unbound free BTC-PEG-BTC. To prepare ASC-seeded gels, cells of at different concentrations (5000-50000/gel) were added to PEG-fibrinogen mixture before the initiation of gelation with thrombin. The cell-gel mixture was placed in a 12 well plate and incubated at 37° C. for 10 minutes. After complete gelation, the PEGylated fibrin gels were washed twice with HBSS and incubated with α-MEM (alpha minimal essential media) supplemented with 10% FBS, antibiotic-antimycotic (100 U/ml of Penicillin G, 100 μg/ml streptomycin sulfate and 0.25 μg/ml Amphotericin B) and 2 mM Lglutamine (Invitrogen, Carlsbad, Calif.), in a 5% CO2 humidified incubator at 37° C.

Morphological Analysis and Viability of ASC in PEGylated Fibrin Gel

ASC seeded at different concentrations (5000-50000 cells) in PEGylated fibrin gel were observed and photomicrographs were taken at different time points (1, 3, 5 and 7 days) using an Olympus IX71 inverted microscope equipped with reflected fluorescence system and DP71 digital camera (Olympus America Inc, Center Valley, Pa.). At similar time points growth media was removed and 50 μl MTT (3-(4,5-dimethylthiozole-2-yl)-2,5-diphenyltetrazolium bromide, Sigma-Aldrich, St. Louis, Mo.) solution (5 mg/ml) was added to each gel and incubated for 5 hours in a 5% CO2 humidified incubator at 37° C. After incubation the MTT solution was removed and 500 μl of isopropyl-acetone mixture (1:1) was added and allowed to incubate for 30 minutes to solubilize and extract the formazan complex. The gel-solvent mixture was then centrifuged at 2700×g for 10 minutes and the supernatant was collected and added to individual wells of a 24 well plate. Absorbance of the supernatants and isopropyl alcohol-acetone mixture (reagent blank) was measured at 570 nm with 630 nm as reference using Molecular Devices Spectramax M2 Microplate Reader (Molecular Devices, Sunnyvale, Calif.). The cell number associated with PEGylated fibrin gel was determined relative to the standard absorbance value obtained from known numbers of viable ASC.

Immunocytochemical Analysis of ASC Seeded PEGylated Fibrin Gels

Immunostaining of ASC in PEGylated fibrin gels. Before cryosectioning, gels (day 11) were cryopreserved using gradient sucrose cryopreservation technique. Briefly, the gels were washed with HBSS (twice, 5 minutes), fixed with 4% paraformaldehyde (PFA, EMS, Hatfield, Pa.) treated serially with increasing concentrations of sucrose (from 5% and 20%) and then incubated overnight with 20% sucrose at 4° C. The sucrose treated gels were embedded in a 20% Sucrose-Histoprep™ (Fisher, Pittsburgh, Pa.) mixture (2:1) and flash frozen. Sections, 10-12 μm thick, were cut using a cryostat (Leica Microsystems, Nussloch, GmbH), washed with sterile HBSS and fixed with 4% PFA for 20 minutes. Non specific Fc receptor mediated blocking sites were blocked by incubating the sections for 40 minutes-1 hr with 1% BSA (bovine serum albumin) in HBSS containing 0.01% Triton X 100 and washed twice (5 minutes) with HBSS. To assess the endogenic immunophenotype, sections were stained with anti rat CD31 (PECAM-1, 8 μg, R&D Systems, Minneapolis, Minn.) and von Willebrand factor (vWF, 10 μg/ml, Millipore, Billerica, Mass.) specific monoclonal primary antibodies. For identifying pericyte immunophenotype, rat specific monoclonal antibodies specific to Chrondroitin sulfate proteoglycan (NG2, 20 μg/ml, Millipore, Billerica, Mass.), platelet derived growth factor receptor beta (PDGFRβ, 10 μg/ml, R&D Systems, Minneapolis, Minn.) and alpha smooth muscle actin (α-SMA, 8 μg/ml, Abcam, Cambridge, Mass.) antibodies were used. The sections were subjected to single or double immunofluorescent staining by incubating with a monoclonal primary antibody or mixture of two antibodies targeted towards two different antigens at 4° C. overnight. Following incubation of unconjugated primary labeled antibodies, sections were washed twice (5 minutes) with HBSS and incubated with 5 μg/ml host species specific Alexa fluor 488 and/or Alexa fluor 594 secondary antibodies (Invitrogen, Carlsbad, Calif.) for 45 minutes at 4° C. Finally, the sections were washed twice (5 minutes) and nuclei stained with Hoechst 33342 (Invitrogen, Carlsbad, Calif.). Non-specific fluorescence was determined using sections incubated with respective fluorophore labeled secondary antibodies.

Fluorescent and confocal microscopic morphological analysis. Epifluorescence of cells and gel sections were observed using Olympus IX71 inverted microscope equipped with reflected fluorescence system (Olympus America Inc, Center Valley, Pa.). Photomicrographs were taken using DP71 digital camera and image overlay was carried out using DP controller application software. Three-dimensional images, were taken using an Olympus FV-500 Laser Scanning Confocal Microscope (Olympus America Inc.), equipped with three channel detection system for fluorescence, a differential interference contrast image (DIC) laser light source and Zstepper motor. The three dimensional stereoscopic images and movie were generated from a series of Z-stacked photomicrographs around the Z-axis using Fluoview and Tiempo Ratio Imaging software and final images processed using Image J software (image processing and analysis in Java, NIH, Bethesda, Md.).

RNA Isolation and Real Time Polymerase Chain Reaction (RT-PCR)

Total RNA from ASC in PEGylated fibrin gel at 1, 3, 5, 7 and 11 days were isolated using Trizol LS reagent (Invitrogen, Carlsbad, Calif., USA) with modifications. Gels were rinsed with HBSS and carefully removed from the culture well. Four gels from each time were pooled together, minced, 16 ml of Trizol LS reagent was added and incubated for 10-15 minutes in ice. Following incubation 8 ml of chloroform was added, mixed and the aqueous phase separated by centrifugation. The RNA was then purified using mini spin columns. The concentration and quality of the purified RNA was determined at OD260/280 using a NanoDrop spectrometer (Nanodrop Technologies, Inc., Wilmington, Del.). Complementary DNA was synthesized from 150 ng of total RNA, in duplicate, using SuperScript™ III first strand synthesis supermix with oligo-dT primers (Invitrogen, Carlsbad, Calif., USA). A control lacking the RNA sample was synthesized to detect the random production of cDNA through contaminants. Oligonucleotide primer sequences specific to endothelial (CD31 and vWF) and pericyte markers (NG2 and PDGFRβ) were purchased from SA Biosciences (Frederick, Md.). Master mixes containing 200 nM of forward and reverse primers with SYBR®GreenERT™, qPCR supermix (Invitrogen, Carlsbad, Calif.) and the synthesized cDNA were added to appropriate wells. RT-PCR was carried out using a Bio-Rad CFX96 thermal cycler system (Bio-Rad, Hercules, Calif.). mRNA expression levels were normalized to glyceraldehye-3-phosphate dehydrogenase (GAPDH). Fold increase in expression levels for each endogenic and pericyte specific gene was normalized to the expression levels of control passage 2 ASC. Fold increase in expression levels for each gene was determined by 2-ΔΔCT method.

Impregnation of ASC Loaded Chitosan Microspheres in PEGylated Fibrin and Collagen Gels Loading ASC into chitosan microspheres. Chitosan microspheres (CSM) were prepared by water in oil emulsification process along with an ionic coacervation technique using our previous described protocol. Prepared CSM were sterilized using absolute alcohol and washed (×3) with sterile water to remove residual salts. ASC were loaded into CSM at 10000 cells/mg using our culture insert technique as previously described. Before culturing ASC in CSM, the cells were cytoplasmically labeled with Quantum dot (Qdot) nanocrystals 565 using Qtracker cell labeling kit (Invitrogen, Carlsbad, Calif., USA). Cells were labeled according to manufacturer's instructions, briefly; 2 μl of labeling solution containing 10 nM of Qdots was incubated for 5 minutes at 37° C. and to this solution 200 μl of MesenPRO media was added and vortexed. To this solution mixture 1 ml of cell suspension ($1 \times 10^6$ cells/ ml) was added and incubated for 45 minutes at 37° C., 5% $CO_2$. Following incubation labeled cell suspension was diluted with MesenPRO media to a final concentration of $5 \times 10^4$ cells/200 µl and seeded over sterilized CSM (5 mg), spread over culture insert of 8 µm pore size membrane (24-well format, BD Falcon, Franklin Lakes, N.J.) and incubated for 24 hours in a humidified incubator at 37° C. and 5% $CO_2$.

Impregnation procedure. ASC (with and without Qdot label) loaded CSM (5 mg) were collected and mixed with PEGylated fibrin gel matrix (prepared as described earlier). The PEGylated fibrin-ASC-CSM mixture was added to a 12 well plate and incubated for 10 minutes at 37° C. In another experimental setup ASC (with and without Qdot label) loaded CSM (5 mg) were collected and impregnated into collagen type I gels following our previous procedure. Briefly, type 1 collagen (5 mg/ml, Travigen, Gaithersburg, Md.) from rat tail tendon was fibrillated by adjusting the pH to 6.8-7.0 using 100 µl of Dulbecco's phosphate buffered saline (DPBS) and 23 µl of 1N NaOH. The fibrillated collagen-ASC-CSM mixture was added to a 12 well plate and incubated for 30 minutes at 37° C. Following complete gelation both the gels (PEGylated fibrin and collagen gels) were incubated at 37° C., 5% $CO_2$. Release of cells was observed for 8 days in case of PEGylated fibrin gels, while in collagen gels cells were observed for 12 days and light microscopic pictures were taken at different days using Olympus IX71 inverted microscope equipped with reflected fluorescence system. To track cells and show their release into the gels fluorescence micrographs were taken on day 6 in both the gels.

Development of Bilayered PEGylated Fibrin—(ASC-CSM)—Collagen Gel Constructs

To develop the bilayer construct, PEGylated fibrin gel was prepared as previously described and added to a 6 well culture insert. Over the surface of the PEGylated fibrin gel 5 mg of ASC-loaded chitosan microspheres (10000 cells/mg) suspended in culture media (200 µl) was seeded onto the gel. After the microsphere have settled over the gel, fibrillated type 1 collagen, prepared as previously described was carefully applied over the PEGylated Fibrin—(ASC-CSM) platform before gelation. After which the whole construct was placed for 30 minutes at 37° C. to achieve complete gelation of collagen matrix. The final bilayered construct consisted of PEGylated Fibrin—(ASC-CSM)—Collagen gel matrix, with collagen gel on the top surface, PEGylated fibrin gel on the bottom and the ASC loaded CSM sandwiched in the interface. The entire bilayered construct was incubated at 37° C., 5% $CO_2$ for 12 days, during which cells released into the gels, were observed and photomicrographs were taken at different days to assess the morphology of the released cells into the gel matrix.

Results

Undifferentiated ASC

The phenotype of undifferentiated ASC has been described with respect to cell surface marker expression measured with FACS. These cells are positive for CD49d, CD54, CD71, CD90 and STRO-1. Prior to the utilization of a particular cell population the positive expression of these five markers was confirmed using immunocytochemical staining. An example result for the cell populations used in this study is shown in FIG. 13.

ASC Growth Characteristics within PEGylated Fibrin

Much like bone marrow-derived MSCs, ASC demonstrate the ability to proliferate and express a characteristic phenotype within PEGylated fibrin gels. FIG. 14 shows the dependency of cell seeding density and culture time on the resulting cell morphology. ASC began to exhibit cellular extensions by day 3. These extensions were more pronounced in cultures with >10,000 cells/ml. Over time the cellular extensions progressed with the formation of dense multicellular networks. By day 7, ASC at all seeding densities demonstrated extensive network formation which was greatest at the highest cell density. Proliferation was assessed over the same timecourse using the MTT assay. (FIG. 5) Proliferative activity increased over the seven day study for all seeding densities and was dependent on the initial density.

ASC Phenotype and Genotype within PEGylated Fibrin

The endothelial cell markers, CD31 and vWF were used to establish the identity of cells expressing an endothelial cell genotype and phenotype. RT-PCR demonstrated that over the 11 day timecourse, there was a dramatic upregulation of endothelial cell markers relative to the housekeeping gene. Specifically, CD31 was upregulated 25 fold over controls while vWF was up 42 fold over controls. (FIG. 15) The immunohistochemical staining confirmed the presence of the expressed protein for both CD31 and vWF. (FIG. 7A-7D) Confocal images of stained sections confirm that both markers are expressed on multicellular networks generated from day 11 samples. What was demonstrated is that the CD31 is more closely associated with the cell nucleus than the vWF. This may be due to the fact that CD31 is expressed on endothelial cell membranes, where vWF may be secreted from the cell and maintained within the fibrin network. The pericyte markers, NG2, PDGFRβ and α-smooth muscle actin were used to track the differentiation of ASC towards a pericyte, or mural cell, phenotype. RT-PCR after 11 days in culture demonstrated that the markers, NG2 and PDGFRβ, were upregulated by 6 fold and 9 fold, respectively, relative to controls. It is important to note here that undifferentiated ASC also express a basal level of PDGFRβ which was approximately 5 fold greater than controls. This value declined as the culture progressed reaching a minimum at day 7 prior to an increase at day 11. Immunohistochemistry revealed that multicellular networks at day 11 exhibited expression of both NG2 (FIG. 7E-7H) and α-SMA (FIG. 7I-7L) Further, a 3-D Z-stack animation was created from sections stained with vWF and α-SMA individually to observe the tube architecture formed in the fibrin gels. The co-localization of these markers typically demonstrated that α-SMA occupied a position on the exterior of the tube relative to vWF. This indicated that the cell populations expressing endothelial and pericyte markers are separate with the pericyte markers occupying a pericellular position within the growing network.

ASC Migration from Chitosan Microspheres

Figures 16A, 16B, 16C, 16D, 16E, 16F:
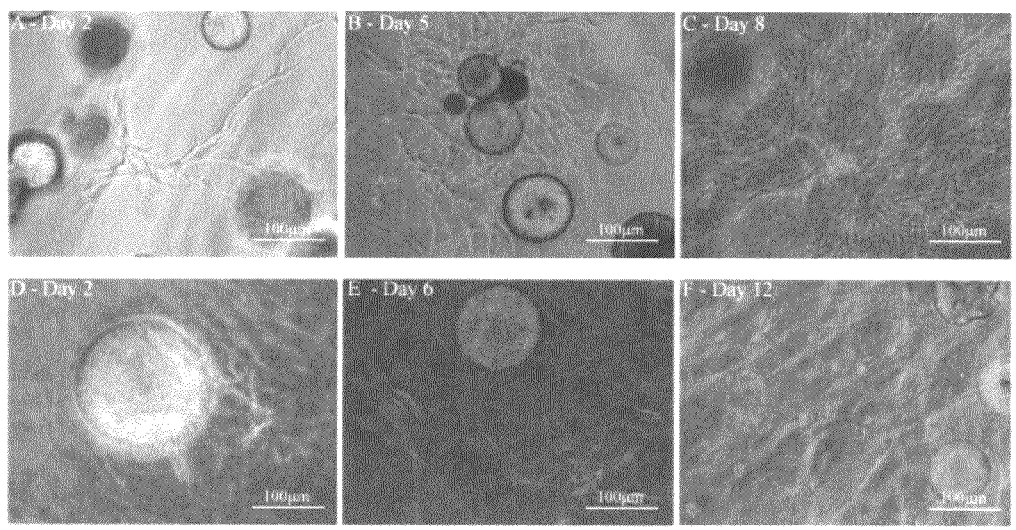
Figures 17A, 17B, 17C, 17D, 17E, 17F:
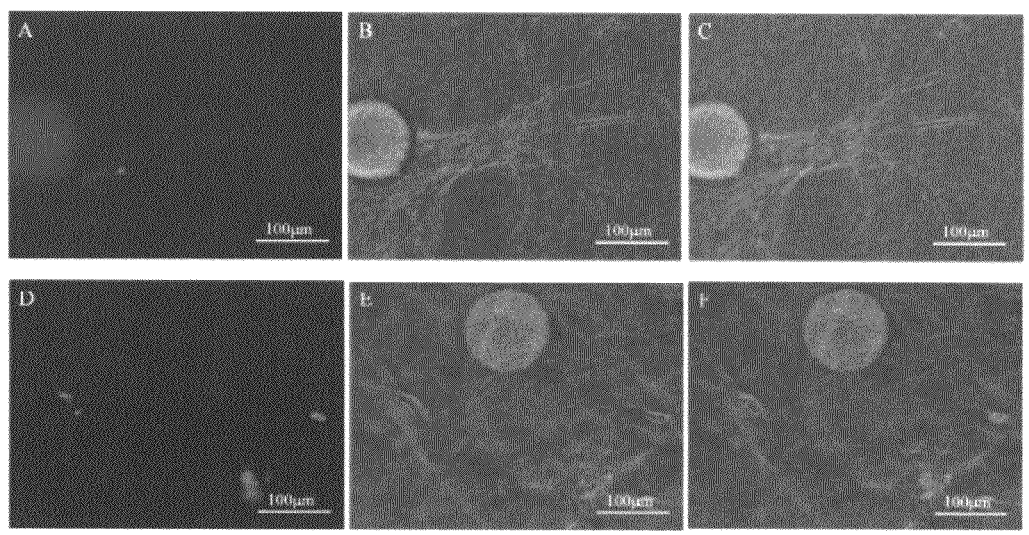
Figures 18A, 18B, 18C, 18D, 18E, 18F, 18G, 18H:
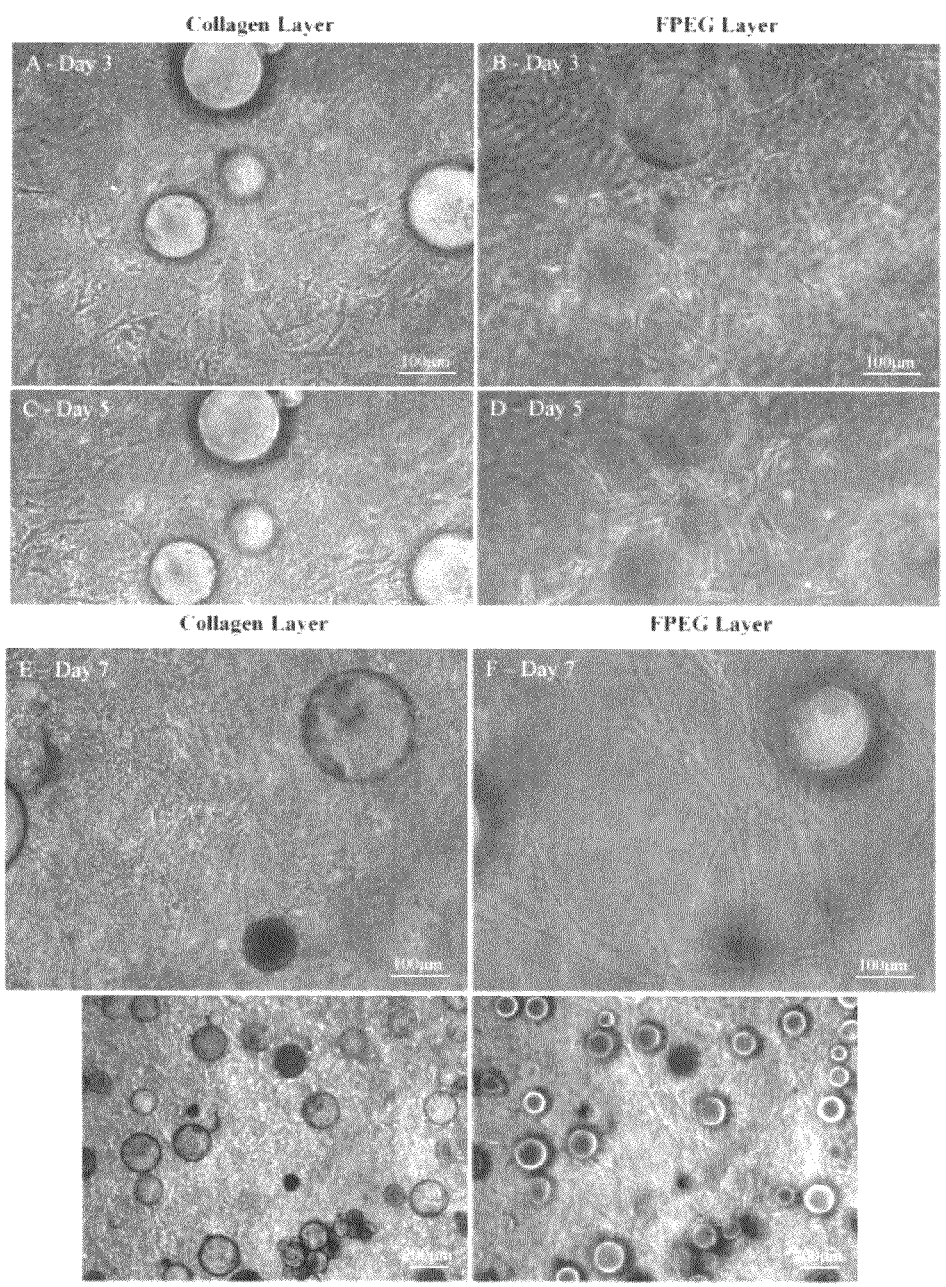
Figures 18A, 18B, 18C, 18D, 18E, 18F, 18G, 18H:
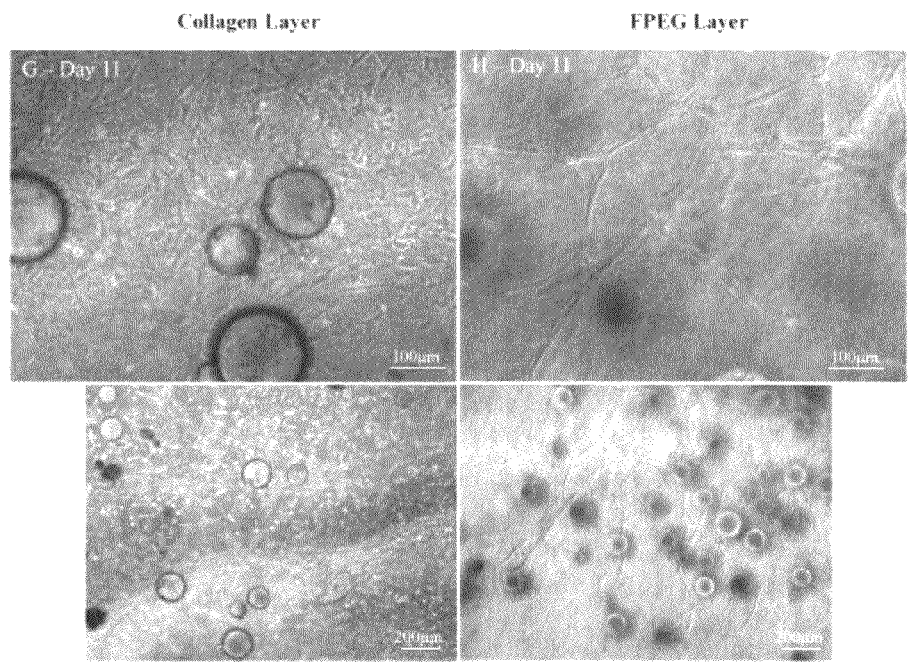

As shown in FIGS. 7 and 16, cells that had been seeded onto chitosan microspheres were able to migrate though either PEGylated fibrin (FIG. 16A-C) or collagen (FIG. 16D-F). Migration was seen in both gels as early as day 2 after seeding. Migration and/or proliferation continued throughout the times monitored (day 8 for PEGylated fibrin and day 12 for collagen). ASC migrating into the PEGylated fibrin demonstrated the characteristic tubular morphology as seen in the gel matrix alone, while ASC migrating through the collagen matrix had a spindleshaped morphology.

When ASC were pre-labeled with Qdot 565 nanocrystals and visualized after 6 days in culture, the labeled cells could be clearly seen as distinct from the chitosan microspheres. The fluorescent images as well as the brightfield overlay for migration into both PEGylated fibrin (FIG. 17A-C) and collagen (FIG. 17D-F) are shown. This result provides evidence that the ASC are able to migrate from the embedded microspheres and into either collagen or PEGylated fibrin.

Matrix-Based Morphology of ASC

FIG. 17 consists of a series of light microscopy images over an 11 day timecourse as ASC grow out of chitosan microspheres into either collagen or PEGylated fibrin. The cells that had been cultured on the surface of microspheres were "sandwiched" between the two different gel layers. This type of experimental setup allowed for the independent investigation of the effects that the matrix environment had on cell migration and differentiation. Cells were clearly able to leave the microsphere surface and migrate into either the collagen gel or the PEGylated fibrin. Cells in both gel layers were evident from day 3 until the end of the culture period. The morphology of the migrated ASC were dramatically different in the two gel layers. In the collagen gels, the cells exhibited a spindle-shaped morphology similar to what was seen in the collagen gel layer by itself. In the PEGylated fibrin gels, the cells demonstrated multicellular tubular networks analogous to those in the PEGylated fibrin layer alone. In a number of the figures, it can be clearly seen that the same microsphere population is shown either from the underside (PEGylated fibrin, FIGS. 18B, D and F) or the top side (collagen, FIGS. 18A, C and E). This indicates the close proximity of the two cell phenotypes as well as the fact that cells on the same bead can exhibit two distinct phenotypes. The cells in the PEGylated fibrin were able to form extended networks that spanned the dimensions of the acquired image. This result provides evidence for the purely matrix-driven differentiation of ASC in either collagen or PEGylated fibrin.

Therefore, the present invention is well adapted to attain the ends and advantages mentioned as well as those that are inherent therein. It should be understood, however, that the description of specific example embodiments is not intended to limit the invention to the particular forms disclosed, but on the contrary, this disclosure is to cover all modifications and equivalents as defined by the appended claims. While numerous changes may be made by those skilled in the art, such changes are encompassed within the spirit of this invention as illustrated, in part, by the appended claims.

What is claimed is:

1. A method of preparing a dermal equivalent comprising:
   providing a synthetic hydrogel matrix comprising at least a first synthetic hydrogel layer and a second synthetic hydrogel layer, wherein the first synthetic hydrogel layer comprises at least one material selected from the group consisting of fibrin, PEGylated fibrin, hyaluronic acid, and any combination thereof and wherein the second synthetic hydrogel layer comprises at least one material selected from the group consisting of collagen I, collagen II, collagen III, collagen IV, collagen V, fibronectin, tenascin, vitronectin, glycosaminoglycans, and any combination thereof;
   isolating a population of mesenchymal stem cells from a source; and
   differentiating at least one of the mesenchymal stem cells towards a dermal fibroblast and at least one of the mesenchymal stem cells towards a blood vessel cell by introducing the population of mesenchymal stem cells between the first and second synthetic hydrogel layers.

2. The method of claim 1 wherein the source is a patient for whom the dermal equivalent is prepared.

3. The method of claim 1 wherein the mesenchymal stem cells comprise adipose derived stem cells.

4. The method of claim 1 wherein the first synthetic hydrogel layer comprises PEGylated fibrin.

5. The method of claim 1 wherein the mesenchymal stem cells are introduced on microcarriers.

6. The method of claim 1 wherein the second synthetic hydrogel layer comprises collagen I.

7. The method of claim 1, wherein the synthetic hydrogel matrix is free of soluble growth factors.

* * * * *